United States Patent

Hansson et al.

[11] Patent Number: 5,816,813
[45] Date of Patent: Oct. 6, 1998

[54] IMPLANT FIXTURE PROVIDED WITH MICRO-THREADS

[75] Inventors: Stig Gustav Vilhelm Hansson, Askim; Stig Göste Wennberg, Angered, both of Sweden

[73] Assignee: Astra Aktiebolag, Sodertalje, Sweden

[21] Appl. No.: 411,736
[22] PCT Filed: Oct. 1, 1993
[86] PCT No.: PCT/SE93/00788
§ 371 Date: May 11, 1995
§ 102(e) Date: May 11, 1995
[87] PCT Pub. No.: WO94/07428
PCT Pub. Date: Apr. 14, 1994

[30] Foreign Application Priority Data

Oct. 5, 1992 [SE] Sweden .................................. 9202911

[51] Int. Cl.⁶ ...................................................... A61C 8/00
[52] U.S. Cl. ............................................................ 433/174
[58] Field of Search .................................... 433/173, 174, 433/221, 224, 225; 606/65, 66, 73

[56] References Cited

U.S. PATENT DOCUMENTS

| | | |
|---|---|---|
| 4,103,422 | 8/1978 | Weiss et al. . |
| 4,713,004 | 12/1987 | Linkow et al. .......................... 433/174 |
| 5,000,686 | 3/1991 | Lazzara et al. .......................... 433/174 |
| 5,022,860 | 6/1991 | Lazzara et al. .......................... 433/174 |
| 5,259,398 | 11/1993 | Vrespa .................................. 606/67 X |

*Primary Examiner*—Nicholas D. Lucchesi
*Attorney, Agent, or Firm*—White & Case

[57] ABSTRACT

The present invention relates to an implant having a body with at least one generally cylindrical part to be implanted into bone tissue. The cylindrical part is at least partly provided with threads (2) having a height between 0.02 mm and 0.20 mm.

8 Claims, 1 Drawing Sheet

IMPLANT FIXTURE PROVIDED WITH MICRO-THREADS

TECHNICAL FIELD OF THE INVENTION

The present invention relates to an element comprising at least one cylindrical part to be implanted into bone tissue.

BACKGROUND TO THE INVENTION

There are two kinds of main systems for endo-osseous dental implants which are commonly used today.

One system utilizes fixtures provided with threads which are threaded into a hole drilled into the jaw-bone. This system can be exemplified by the so-called Brånemark system™. This system comprises both threaded fixtures which are to be screwed into holes which have been provided with threads in advance and self-tapping fixtures which are screwed into a non-pretapped hole drilled in the jaw-bone.

The other system commonly used can be exemplified by the so called IMZ-implant, which utilizes a cylinder provided with a rough surface serving as a fixture and which gently is tapped into a bore-hole in the jaw-bone. The roughness of the surface has no specific orientation.

The threaded fixtures have some important advantages, a major one being a result of the fact that the main loads in the clinical situation are axial loads. Threaded implants are very well suited to support axial loads and this may be particularly important in the initial stages of the osseointegration process in which it is important that the implant is fully stable and as immovable as possible in the bore-hole. The term "osseo-integration" as coined by Prof Brånemark and his coworkers in Gothenburg during the seventies and as used here refers to the close apposition between bone tissue and implants that for instance may be obtained by using implants made of titanium.

There are however some inherent disadvantages in this construction, one of the major ones being the time and the care needed to screw a self-tapping implant into a hole. If the hole also has to be provided with threads in advance, the total period of time needed for the operation of course will be much greater. Although a conventional threaded implant conceivably could be tapped into a hole having almost the same diameter as the major diameter of the threads, the distance the bone tissue would have to grow into the threads would be excessive and the time needed for the osseo-integration process would be long.

The rough-surfaced cylindrical implant is very simple to insert and the time needed for this is short. It may however happen that implants having this design gets stuck in the bore-hole before the implant is fully inserted, which may result in an unacceptable trauma to the bone tissue, both if the implant is inserted entirely by force and if the implant is extracted by force. Both the initial and the final stability of the implant will be less than the initial and the final stability of a threaded implant.

SHORT DESCRIPTION OF THE INVENTIVE CONCEPT

The object of the invention is to provide an implant which combines the advantages of the two above systems whilst eliminating the disadvantages thereof.

This object is achieved in that an endo-osseous implant is provided with the features set forth in the appended main claim.

Preferred embodiments are set forth in the appended dependent claims.

SHORT DESCRIPTION OF THE APPENDED DRAWINGS

DETAILED DESCRIPTION OF PREFERRED EMBODIMENTS OF THE INVENTION

Figure 1:
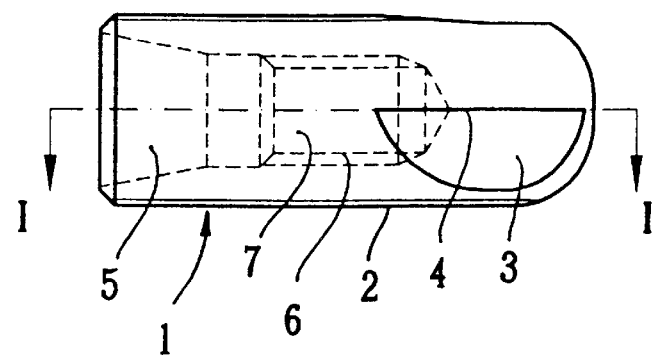
FIG. 1 shows an overall view of an implant according to the invention.
Figure 2:
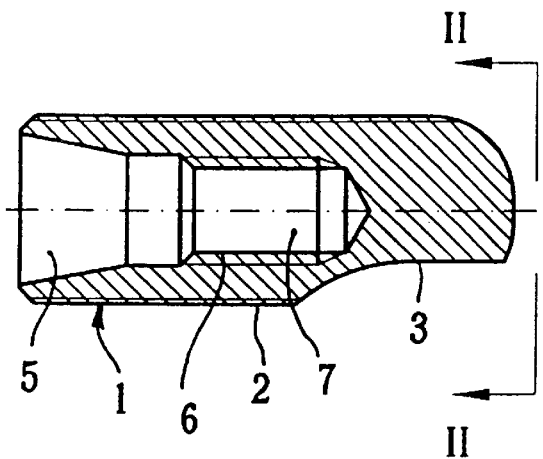
FIG. 2 shows a section of the implant in FIG. 1 taken along the the line I—I.

A preferred embodiment of the invention comprises an implant having a generally cylindrical body 1 for insertion into a bore-hole in bone tissue. The envelope surface of the body 1 is provided with very small threads 2, herein called micro-threads since their dimensions are in the micrometer range. These threads will allow the implant to function as a screw. The forward end or the tip of the screw is provided with three cutting edges 4 in conjunction with chip-collecting cavities 3. A result of the presence of the chip-collecting cavities is that parts of the cylindrical part are not provided with threads. In view of the way the implant is intended to function, an area, which is sufficient to allow the implant to function as a screw, must be provided with threads. In this preferred embodiment the tip of the body furthermore is rounded in order to initially leave some space below the screw for any loose bone chips etc which might impede the full insertion of the screw. The bottom of the bore-hole is normally slightly conically shaped due to the shape of the drills normally used.

The cutting edges 4 and the chip-collecting cavities 3 will allow the screw, if necessary, to function as a self-tapping screw for cutting new threads or for adjusting threads already cut in the tissue.

The other end of the screw is, as is quite conventional in the art, provided with a longitudinal bore for the attachment of an abutment for bridging the soft tissue covering the bone tissue and for the attachment of a prosthesis. The inner part 7 of the bore is cylindrical and provided with interior threads 6 and the outer part 5 of the bore is conically flaring in order to accommodate a conically tapering attachment part of an abutment ending in a cylindrical, threaded end portion.

Figure 4:
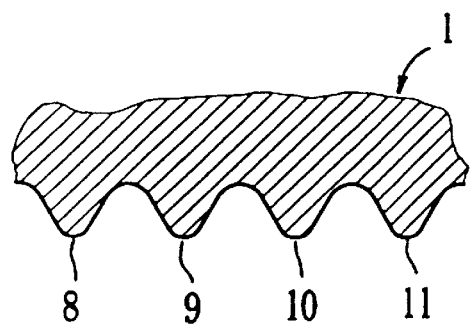
FIG. 4 shows a first preferred embodiment of the micro-threads and FIG. 5 a second preferred embodiment of the microthreads.
Figure 3:
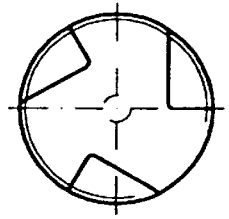
FIG. 3 shows an end view according to the line II—II in FIG. 2.
Figure 5:
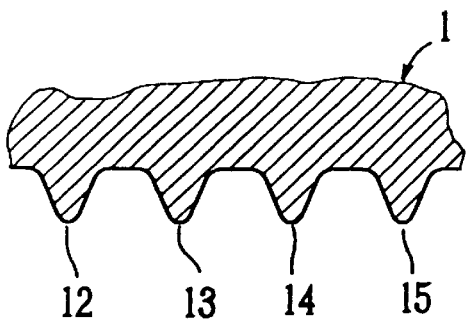

FIGS. 4 and 5 illustrate two different embodiments of the invention. The thread shown in FIG. 4 is 0.1 mm high and the distance to the adjacent thread (crest to crest) is 0.2 mm. The screw is triple-threaded, which means that the pitch of the thread is 0.6 mm. The reason for the triple-threaded design rather than a single-threaded design is that the time needed for screwing the implant into the bore will be less with a multiple-threaded screw. The angle between the flanks of a thread is 45°. The threads have a rounded design in order to avoid, or at least minimize, stress-concentrations in the bone tissue around the threads.

The thread shown in FIG. 5 differs from the thread in FIG. 4 mainly in that the angle between the flanks is 60° instead of 45°.

Generally, the height of the micro-threads may be within the range of 0.02–0.20 mm. In a preferred embodiment the height may vary between 0.02 and 0.15 mm, in a more preferred embodiment between 0.05 and 0.15 and in a most preferred embodiment the height is 0.1 mm. The number of threads is optional but may for instance vary between 1 and 5. In a preferred embodiment the distance between adjacent threads, crest to crest, is twice the height of the threads.

The threads can be regarded as a defined, oriented roughness which is in the same size range as the prior art non-oriented surface roughness, for instance of the kind that can be obtained by plasma-spraying, which is a conventional technique for obtaining a surface roughness on implants.

A non-oriented roughness having smaller dimensions, for instance obtained by blasting techniques, may be superimposed on the threads.

A bio-mechanical study, (Hansson S.: On the role of surface roughness for load bearing bone implants: The retention potential of a micro-pitted surface as a function of pit size, pit shape and pit density. Thesis, Centre for Biomech., Chalmers Univ. of Technol. and Gothenburg Univ., Preprint 1991:4, Gothenburg) has shown that, with a roughness of this size, a retention is obtained which is similar to the retention obtained with more coarse threads.

The implant can be used as both a cylindrical, rough-surfaced implant and as a threaded implant depending on what is suitable from a medical point of view and depending on the preferences of the dentist or surgeon.

If the implant is used as a cylindrical implant, the implant can be lightly tapped into a hole which has the same or almost the same diameter as the major diameter as the implant (the diameter preferably should not be larger) in the same way as a conventional implant. This normally can be done relatively quickly. However, should the implant get stuck half-way, which sometimes may happen, the surgeon may choose between unscrewing the implant, or screwing the implant fully into the hole. This can be done without exposing the surrounding bone tissue to the kind of trauma that would have been the result if the implant were to be extracted forcibly or hammered into place by force.

New bone tissue will rapidly grow into the microthreads due to the low height of the threads and a retention which is considerably better in the axial direction than in the rotational (tangential) direction will be obtained relatively quickly. This is of course a result of the fact that the threads are oriented circumferentially. Compared to an implant provided with threads, an implant with a non-oriented surface roughness in the size range in question will not offer the same retention area (i. e. the area which is interlocking with the bone tissue) perpendicularly to the axial direction and consequently will not offer the same degree of retention.

The design of the implant according to the invention will also permit a very gentle insertion of the implant in the upper jaw, which may be more sensitive than the lower jaw. This is due to the fact that the micro-threaded implant does not require any extensive thread-cutting operations in the sometimes relatively fragile bone tissue in the upper jaw and either can be inserted as a self-tapping screw with a minimum of cutting action or, more importantly, can be just pushed or gently tapped into a bore-hole in the upper jaw.

A further advantage of the invention is that also small, narrow implants will have a maximal stiffness or rigidity which may be important in view of a correct transfer of the main, axial loads to the surrounding bone tissue, since the the threads will form a comparatively small portion of the entire cross-section of the implant.

As mentioned above, the implant also can be used in the same way as a conventional screw-threaded implant, in which case the hole bored in the bone tissue should have a diameter corresponding to the minor diameter of the thread or somewhat larger. In the latter case, the force needed to cut the threads in the bone tissue will be less.

It should be noted that the invention can be varied in many ways within the scope of the appended claims. It should for instance be emphasized that the invention is not limited to dental implants and that the invention could be applied to any generally cylindrical implant to be inserted into a generally cylindrical bore. Generally cylindrical in this context should be read as having parts coinciding with the envelope surface of a cylinder circumscribing the implant. A screw-shaped implant having a fluted body (in similarity with a tap) thus for instance is to be within the scope of the protection as conferred by the appended claims.

We claim:

1. An implant fixture capable of being tapped or screwed into a bore-hole in bone tissue, the fixture comprising:
    a body having at least one part with a generally cylindrical surface; and
    threads disposed on the cylindrical surface, no thread having a height greater than about 0.20 mm.

2. An implant fixture according to claim 1, wherein said threads have a height between 0.02 and 0.15 mm.

3. An implant fixture according to claim 2, wherein said threads have a height between 0.05 and 0.15 mm.

4. An implant fixture according to claim 3, wherein said threads have a height of 0.10 mm.

5. An implant fixture according to any one of the preceding claims, wherein adjacent threads are separated by a crest-to-crest distance that is twice the height of the threads.

6. An implant fixture according to claim 5, wherein the threads are multiple threads, preferably triple threads.

7. An implant fixture according to claim 5, wherein each thread has a flank and the angle between the flanks of the thread is 45°.

8. An implant fixture according to claim 5, wherein each thread has a flank and the angle between the flanks of the thread is 60°.

* * * * *

UNITED STATES PATENT AND TRADEMARK OFFICE
CERTIFICATE OF CORRECTION

PATENT NO. : 5,816,813
DATED : October 6, 1998
INVENTOR(S) : Hansson et al.

It is certified that error appears in the above-indentified patent and that said Letters Patent is hereby corrected as shown below:

Col. 4, line 47 (claim 7, line 3), and line 50 (claim 8, line 3), change "thread" to --threads--.

Signed and Sealed this

Twenty-seventh Day of July, 1999

*Attest:*

Q. TODD DICKINSON

*Attesting Officer*     Acting Commissioner of Patents and Trademarks